United States Patent [19]

Duloisy et al.

[11] Patent Number: 5,733,042
[45] Date of Patent: Mar. 31, 1998

[54] DEVICE AND METHOD FOR TESTING AN OPTICAL ELEMENT SUBJECTED TO RADIATION

[75] Inventors: Erik Duloisy, Seyssinet; Jean Dijon, Champagnier, both of France

[73] Assignees: Commissariat a l'Energie Atomique, Paris; Etat Francais, Armees, both of France

[21] Appl. No.: 577,384

[22] Filed: Dec. 22, 1995

[30] Foreign Application Priority Data

Dec. 26, 1994 [FR] France .................. 94 15640

[51] Int. Cl.[6] ............ G01N 17/00; G01N 25/00; G01N 25/72
[52] U.S. Cl. ............... 374/57; 374/141; 374/120; 374/164
[58] Field of Search .............. 374/57, 142, 164, 374/120, 137, 5, 141

[56] References Cited

U.S. PATENT DOCUMENTS

| 2,769,893 | 11/1956 | Muller | 374/57 |
|---|---|---|---|
| 2,951,360 | 9/1960 | Sampson et al. | 374/5 |
| 3,222,917 | 12/1965 | Roth | 374/5 |
| 3,258,957 | 7/1966 | Smart | 374/5 |
| 3,378,685 | 4/1968 | Green et al. | 374/5 |
| 4,112,362 | 9/1978 | Hower et al. | 374/137 |
| 4,214,164 | 7/1980 | Traub et al. | |
| 4,620,799 | 11/1986 | Palazzetti et al. | 374/57 |
| 4,747,698 | 5/1988 | Wickramasinghe et al. | 374/164 |
| 4,793,716 | 12/1988 | Wei et al. | 374/57 |
| 4,941,753 | 7/1990 | Wickramasinghe | 374/120 |
| 4,997,287 | 3/1991 | Tittl | 374/142 |
| 5,318,361 | 6/1994 | Chase et al. | 374/57 |
| 5,356,218 | 10/1994 | Hopson et al. | 374/142 |
| 5,441,343 | 8/1995 | Pylkki et al. | 374/164 |
| 5,647,667 | 7/1997 | Bast et al. | 374/57 |

FOREIGN PATENT DOCUMENTS

| 0117447 | 7/1983 | Japan | 374/5 |
|---|---|---|---|
| 1188582 | 10/1985 | U.S.S.R. | 374/57 |
| 1198423 | 12/1985 | U.S.S.R. | 374/5 |
| 2188163 | 9/1987 | United Kingdom . | |

OTHER PUBLICATIONS

Applied Optics, vol. 23, No. 21, Nov. 1984, pp. 3774–3778, Stewart et al., "Laser Damage Test Results, Etc.".
Review of Scientific Instruments, vol. 58, No. 10, Oct. 1987, pp. 1942–1944, "Lawson Thermal Cycling Apparatus, Etc.".

Primary Examiner—Diego F. F. Gutierrez
Attorney, Agent, or Firm—Pearne, Gordon, McCoy & Granger LLP

[57] ABSTRACT

Device and method for testing an optical element (E) to determine ability to withstand heating by a high-energy luminous beam. The contact of a point (11) is applied to the optical element and is heated to a specific temperature to simulate radiation. The contact point includes a dog point having a sectional configuration similar to a track of a simulated radiation beam. The heat can be adjusted and the temperature sensed.

12 Claims, 1 Drawing Sheet

DEVICE AND METHOD FOR TESTING AN OPTICAL ELEMENT SUBJECTED TO RADIATION

FIELD OF THE INVENTION

The invention concerns a device for testing an optical element intended to be subjected to radiation.

BACKGROUND OF THE INVENTION

Certain rays, especially laser rays, have sufficient power able to destroy elements by means of heating, such as lenses or mirrors they traverse or reach, despite the weakness of the portion of their energy they lose in these elements by means of the optical coupling.

Damage may be due to the heating itself which alters the material of the element throughout, or to the stresses it generates in the element between the zones traversed by the ray and the other colder zones, or between layers of different compositions of the element and which causes the appearance of cracks, cleavings, blisterings or similar defects.

A suitable test method consists of irradiating the element by a beam similar to the one it needs to resist in operation. This method is tested and suitable but does have a certain number of drawbacks. First of all, it is difficult to measure the real thermic stress as it is impossible to directly measure the temperature of the beam or that of the test piece at the incoming point of the beam by placing a thermometer there and accordingly it is necessary to carry out an indirect measurement with the aid of physical and mathematical models and the optical coupling of the material. Other parameters, such as the power of the beam, are also difficult to properly measure. Existing test benches are therefore complicated and costly.

Another more basic problem is that the optical absorption at the origin of heating of the element often varies widely according to the temperature of the element and normally increases at high temperatures. The test is then unstable, the heating of the test piece being increasingly faster until it is eventually destroyed, the main consequence of this being that the development of damage cannot be observed in good conditions. Finally, a serious drawback stems from the fact that the end of the test mostly depends on heterogeneities and impurities of the element: in practice, these impurities, which far better absorb the energy of the radiation, are heated to a temperature higher than the rest of the element and favor its destruction. It would de desirable to be rid of this adverse effect by using in the test an element freed of impurities.

SUMMARY OF THE INVENTION

The invention concerns a test device and method in which the effect of the radiation is simulated by a mechanical coupling of the element with a piece playing the role of a hot source which transmits its heat to the element by conduction with improved effectiveness. Thus, tests can be conducted where the temperature of the optical element at the incoming point of the beam is always accurately known without a runaway heating phenomenon occurring, which makes it possible to keep the test constant and spread it over a time as long as desired so as to follow up evolution of destruction. It is also possible to use an element charged with impurities as the temperature imposed by the hot piece in contact is the same for the impurities, which no longer constitute hot focal points, as for the rest of the element. Finally, the measurement of this temperature is extremely easy if, for example, there is a thermometer in the point.

In its most general form, the test device includes a support for fixing the optical element in the test, and a thermic conductive point connected to a mobile adjustable heat source above the support so as to be placed on the optical element.

BRIEF DESCRIPTION OF THE DRAWINGS

The invention is now to be described by way on non-restrictive illustration with the aid of the following figures.

DETAILED DESCRIPTION OF THE PREFERRED EMBODIMENTS

Figure 1:
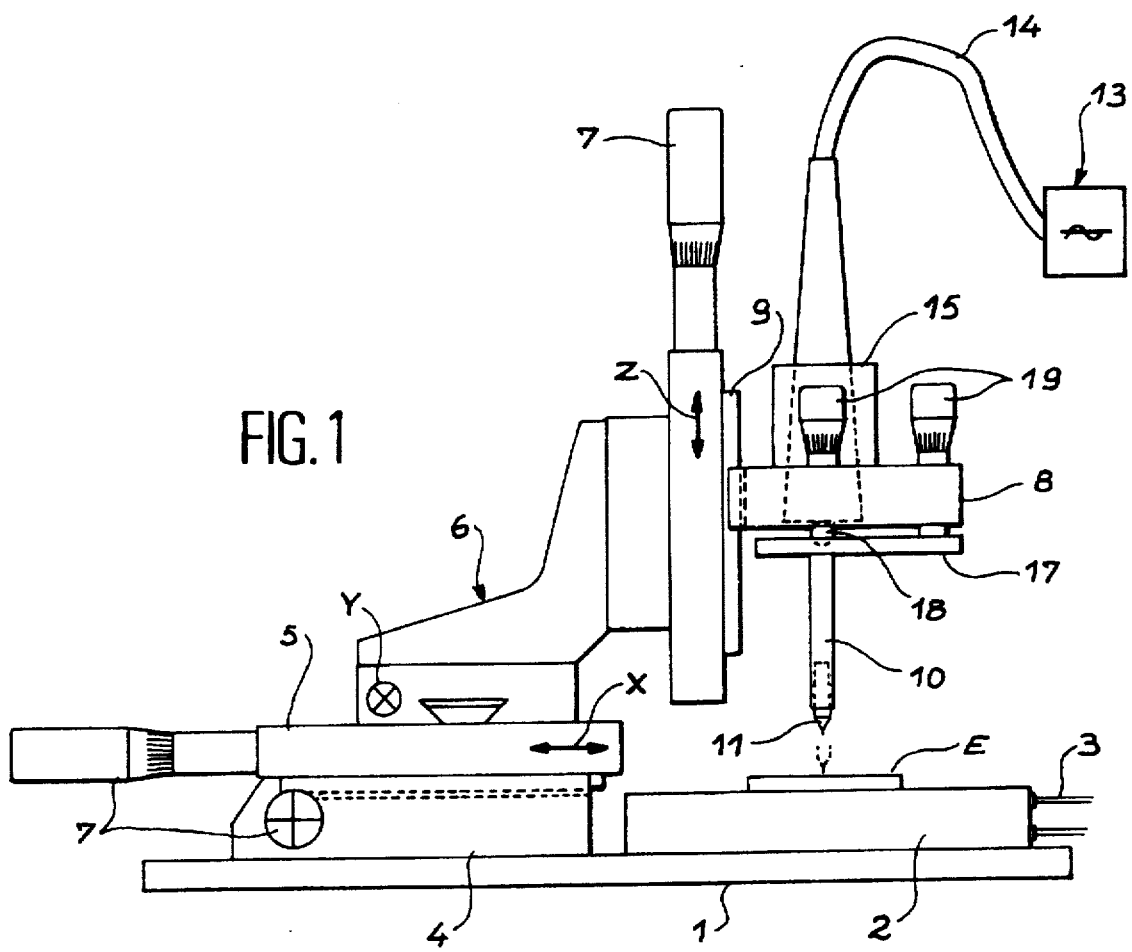
FIG. 1 is a side elevation view of the test device.

The test machine, known as a thermic indenture, includes a support plate 1 on which disposed side by side are a support 2 for the test piece E to be examined and occupied by a thermostat 3, and a lower table 4. This lower table 4, together with an upper table 5 and a bracket 6 successively placed on it, form an X-Y displacement table with current usage in, for example, working machines: the upper table 5 moves onto the lower table 4 perpendicular to the test piece support 2, and the bracket 6 moves onto the upper table 5 parallel to the test piece support 2. These movements are imposed by dovetail slide adjustments. Verniers 7 installed on the tables 4 and 5 ensures these movements with the desired precision. A third vernier 7, situated at the top of the bracket 6, moves a cursor 8 in the direction Z perpendicular to the preceding verniers, that is towards the upper surface of the test piece support 2 and the test piece itself E or in an opposite direction. The cursor 8 can slide on the bracket 6 along another dovetail slide 9.

Figure 2:
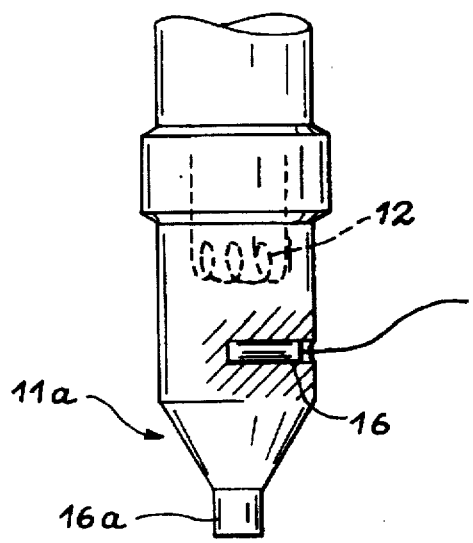
FIGS. 2 and 3 are detailed views of the points used.
Figure 3:
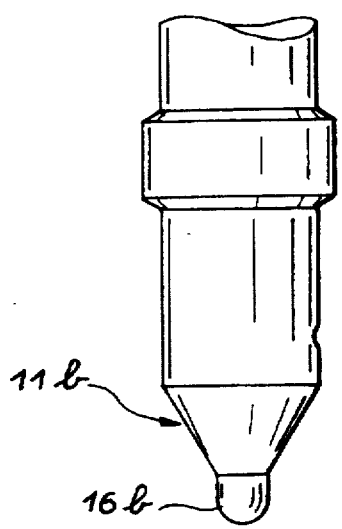

The cursor 8 carries above it a rod 10 directed downwards and having a point 11 at its end, two embodiments of said point being shown on FIGS. 2 and 3. If reference is made to these figures, it can be seen that the point 11 is heated by a resistor 12 it covers and which is connected to the electric grid 13 by a cable 14 whose wires extend into the rod 10. In another embodiment, the resistor 12 may be wound around the rod 10 close to the point 11. An adjustment system 15, which may include a transformer and a rheostat, is added so that the power dissipated by the resistor 12 and thus the temperature of the point 11 can be changed at will. This temperature is measured by a thermometer 16 engaged in a notch of the point 11 and which may consist of one thermal converter end. The thermometer 16 should simply be relatively small so as to avoid compromising the flow of the conductive heat by occupying only a slight volume in the point 11. The point 11 is therefore preferably made of a material having good thermal conductivity and with slight expansion. For example, materials such as aluminum and then molybdenum at low temperatures are recommended.

The point 11 is ended by a dog point whose shape makes it possible to simulate the track of the incident radiation on the test piece E and which may have a circular, square or polygonal section. Moreover, the face touching the test piece E may be flat, as shown with the dog point 16a of FIG. 2, or rounded as shown with the dog point 16b of FIG. 3. In all cases, the surface of the point in contact with the test piece must be polished, regardless of its shape. This polishing preferably ought to be of optical quality. The deposit of an unalterable coating is to be envisaged on this face in contact so as to protect the point 11 from oxidation of the air. Gold can therefore be deposited by means of evaporation.

It may be advantageous, especially in the first case, to also adjust the rotation orientation of the point 11. In this case, the rod 10 is not directly fixed to the cursor 8 but to a shelf 17 and which is suspended from it, for example, by a central pot type joint 18. Two additional verniers 19 linked to the cursor 8 and at a right angle with respect to the joint 18 can then be made to tilt the shelf 17 and the rod 10 around axes X and Y respectively.

The vernier 7 moving the cursor 8 vertically may include a known type of disconnection device which interrupts the descent of the rod 10 the moment the point 11 presses the optical element E with a certain force, regardless of the commands imposed on the vernier 7. Thus, the optical element E is protected against mechanical damage or at least excessive stresses which could interfere with the test.

The test therefore consists of placing the point 11 on the optical element E after having adjusted the power delivered by the resistor 12 and the temperature of the support 2 by the flow and temperature of the liquid traversing the thermostat 3. Contact is maintained for the desired period, after which the rod 10 is removed and the optical element E is withdrawn and examined.

Comparative tests with this indenting machine and conventional laser tests have been conducted on a certain number of test pieces. They revealed excellent convergence of results concerning the extent of damage and the destruction temperature, although in the latter case differences are possible owing to impurities, as explained earlier. Thus, this machine can be effectively used to replace conventional tests.

What is claimed is:

1. A process for testing an optical element intended to be subjected to radiation by simulating the thermal effects of a track of a radiation beam, comprising the steps of:

fixing the optical element on a support, applying a thermal conductive point connected to a heat source onto the optical element, an end of the point being a dog point having a sectional configuration similar to the track of the radiation beam, adjusting a heat power provided by the heat source to the point to correspond to the power radiated by the track of the radiation beam, maintaining the point applied onto the optical element with the adjusted heat power for a predetermined period of time, and adjusting the temperature of the support.

2. A process for testing an optical element according to claim 1, wherein the point has a rounded end.

3. A process for testing an optical element according to claim 1, wherein the point has a flat end.

4. A process for testing an optical element according to claim 1, wherein the point is rotated.

5. A process for testing an optical element according to claim 1, wherein the point has a polished surface in contact with the optical element.

6. A process according to claim 1, wherein the temperature of the optical element is sensed by a thermometer contained in the point.

7. A device for testing an optical element intended to be subjected to radiation by simulating the thermal effects of a track of a radiation beam, comprising:

a support on which the optical element is fixed, a thermal conductive point connected to a heat source and applied onto the optical element, an end of the point being a dog point having a sectional configuration similar to the track of the radiation beam, means for adjusting a heat power provided by the heat source to the point to correspond to the power radiated by the track of the radiation beam, means for maintaining the point applied onto the optical element with the adjusted heat power for a predetermined period of time, and means for adjusting the temperature of the support.

8. A device according to claim 7, wherein a thermometer contained in the point senses the temperature of the optical element.

9. A device for testing an optical element according to claim 7 wherein the point has a rounded end.

10. A device for testing an optical element according to claim 7 wherein the point has a flat end.

11. A device for testing an optical element according to claim 7 wherein the point is rotated.

12. A device for testing an optical element according to claim 7 wherein the point has a polished surface in contact with the optical element.

* * * * *